United States Patent [19]

Seele et al.

[11] Patent Number: 5,106,848
[45] Date of Patent: Apr. 21, 1992

[54] FUNGICIDAL MIXTURE

[75] Inventors: Rainer Seele, Fussgoenheim; Friedrich Loecher, Limburgerhof; Reinhold Saur, Boehl-Iggelheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 599,886

[22] Filed: Oct. 19, 1990

[30] Foreign Application Priority Data

Oct. 21, 1989 [DE] Fed. Rep. of Germany ....... 3935113

[51] Int. Cl.$^5$ ..................... A01N 43/84; A01N 43/64
[52] U.S. Cl. ................................. 514/239.5; 514/383
[58] Field of Search ............................ 514/239.5, 383

[56] References Cited

U.S. PATENT DOCUMENTS

| 4,202,894 | 5/1980 | Pfiffner | 544/105 |
| 4,241,058 | 12/1980 | Pfiffner | 544/105 |
| 4,652,580 | 3/1987 | Janssen et al. | 514/383 |
| 4,906,652 | 3/1990 | Karbach et al. | 514/383 |

FOREIGN PATENT DOCUMENTS

| 0196038 | 10/1986 | European Pat. Off. |
| 2752135 | 5/1978 | Fed. Rep. of Germany |
| 2752096 | 6/1978 | Fed. Rep. of Germany |

*Primary Examiner*—Allen J. Robinson
*Attorney, Agent, or Firm*—Oblon, Spivak, McClelland, Maier & Neustadt

[57] ABSTRACT

A mixture consisting of a) a triazolylmethyldiphenyloxirane derivate and b) fenpropimorph, fenpropidin or tridemorph and which exhibits a synergistic fungicidal action, and methods of combating fungi with this mixture.

6 Claims, No Drawings

FUNGICIDAL MIXTURE

The present invention relates to fungicidal mixtures having a synergistic fungicidal action and methods for controlling fungi with these mixtures.

It is known that 2-(1,2,4-triazol-1-ylmethyl)-2-(4-fluorophenyl)-3-(2-chlorophenyl)-oxirane of the formula

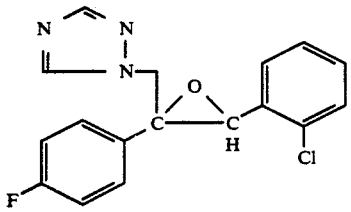

or one of its salts can be used as a fungicide (EP 196 038). It is also known that the active ingredients fenpropimorph, 4-[3-(4-tert-butylphenyl)-2-methylpropyl]-cis-2,6-dimethylmorpholine of the formula

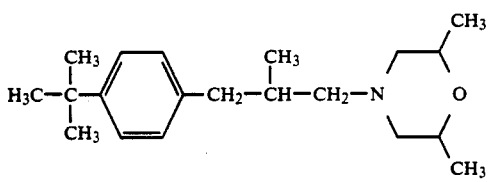

or its salts, fenpropidine, N-[3-(4-tert-butylphenyl)-2-methylpropyl]-piperidine of the formula

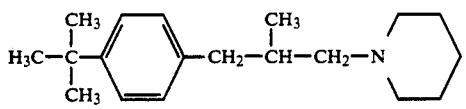

or its salts, or the active ingredient tridemorph, N-tridecyl-2,6-dimethylmorpholine of the formula

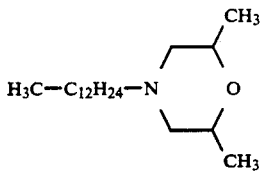

or its salts can be used as fungicides (DE-A 27 52 096, 27 52 135 and 11 65 930).

We have found that a mixture of
a) 2-(1,2,4-triazol-1-ylmethyl)-2-(4-fluorophenyl)-3-(2-chlorophenyl)-oxirane of the formula I

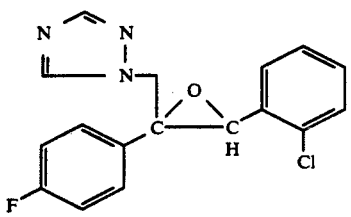

b) a heterocyclic compound of the formula II

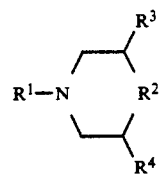

where
$R^1$ is tridecyl ($CH_3$—$C_{12}H_{24}$—) or the radical

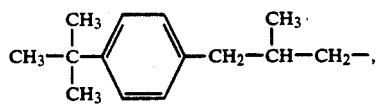

$R^2$ is $CH_2$ or O and
$R^3$ and $R^4$ are each methyl or H, or a plant-tolerated salt or metal complex thereof has a synergistic fungicidal action. The mixing ratio (weight ratio) of the compounds a) and b) is chosen to give a synergistic fungicidal action, for example compound a) and compound b) in a ratio of from 5:1 to 1:5, in particular from 3:1 to 1:3, preferably from 2:1 to 1:2.

2-(1,2,4-Triazol-1-ylmethyl)-2-(4-fluorophenyl)-3-(2-chlorophenyl)-oxirane, component a), may occur in four stereoisomeric forms which have different fungicidal activities. The two cis-isomers, i.e. the enantiomers in which the triazolylmethyl group and the 2-chlorophenyl group are on the same side of the oxirane ring, are preferred. Fenpropimorph occurs in two enantiomeric forms, of which the (—)-enantiomer, which has an S-configuration, is preferred as the active partner. The present invention includes mixtures of pure isomers of the compounds a) and b), in particular mixtures of a cis-enantiomer of 2-(1,2,4-triazol-1-ylmethyl)-2-(4-fluorophenyl)-3-(2-chlorophenyl)-oxirane with the (—)cis-enantiomer of fenpropimorph.

The present invention also includes agents in which the active ingredient component a), 2-(1,2,4-triazol-1-ylmethyl)-2-(4-fluorophenyl)-3-(2-chlorophenyl)-oxirane, is predominantly in the form of the two cis-enantiomers.

Salts are prepared by reaction with acids, for example halohydric acids, such as hydrofluoric acid, hydrochloric acid, hydrobromic acid or hydriodic acid, or sulfuric acid, phosphoric acid, nitric acid or organic acids, such as acetic acid, trifluoroacetic acid, trichloroacetic acid, propionic acid, glycolic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid or 1,2-naphthalenedisulfonic acid.

Complexes can, if desired, contain only one component a) or one component b) or a plurality of components b). It is also possible to prepare metal complexes which contain both components a) and b) together in a mixed complex.

Metal complexes are prepared from the parent organic molecule and an inorganic or organic metal salt, for example the halides, nitrates, sulfates, phosphates, acetates, trifluoroacetates, trichloroacetates, propionates, tartrates, sulfonates, salicylates or benzoates of the metals of main group two, such as calcium or magnesium, and of main groups three and four, such as aluminum, tin or lead, and of subgroups one to eight, such as chromium, manganese, iron, cobalt, nickel, copper or zinc. The subgroup elements of the fourth period are preferred. The metals may have their various valencies. The metal complexes may be mononuclear or polynuclear, i.e. they may contain one or more organic molecular moieties as ligands, for example mixed complexes of 2-(1,2,4-triazol-1-ylmethyl)-2-(4-fluorophenyl)-3-(2-chlorophenyl)-oxirane and fenpropimorph, fenpropidine or tridemorph.

In practice, it is advantageous to use the pure active ingredients a) and b) to which other agrochemical active substances, such as insecticides, acaricides, nematicides, herbicides, further fungicides, growth regulators and/or fertilizers, may also be added.

In general terms, the novel mixtures are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
*Rhizoctonia solani* in cotton,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The compounds are applied by spraying or dusting the plants with a fungicidally effective amount of the mixtures, or treating the seeds of the plants with the mixtures. They may be applied before or after infection of the plants or seeds by the fungi. Either the fungi themselves, or the plants, seed, materials or soil to be protected against fungus attack are treated with a fungicidally effective amount of the mixtures.

Active ingredients a) and b) may be applied one briefly after the other, the mixture thus being formed on the plant or seed.

The novel mixtures can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt % of active ingredient. The application rates are from 0.02 to 3 kg or more of active ingredient per hectare, depending on the type of effect desired. The novel mixtures may also be used for protecting materials (timber), e.g., against *Paecilomyces variotii*. When the mixtures are used for treating seed, generally amounts of from 0.001 to 50, and preferably from 0.01 to 10, g per kg of seed are sufficient.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. A solution of 90 parts by weight of a mixture of compound a) with fenpropimorph and 10 parts by weight of N-methyl-α-pyrrolidone, which is suitable for application in the form of very fine drops.

II. A mixture of 20 parts by weight of a mixture of compound a) with fenpropidin, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, an aqueous dispersion is obtained.

III. A solution of 20 parts by weight of a mixture of compound a) with tridemorph, 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. A solution of 20 parts by weight of a mixture of compound a) with fenpropimorph, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the mixture into water and finely distributing it therein, an aqueous dispersion is obtained.

V. A hammer-milled mixture of 80 parts by weight of a mixture of compound a) with fenpropidin, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel.

By finely dispersing the mixture in water, a spray liquor is obtained.

VI. An intimate mixture of 3 parts by weight of a mixture of compound a) with tridemorph and 97 parts by weight of particulate kaolin. The dust contains 3 wt % of the active ingredient.

VII. An intimate mixture of 30 parts by weight of a mixture of compound a) with fenpropimorph, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of a mixture of compound a) with fenpropidin, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of a mixture of compound a) with tridemorph, 2 parts by weight of the calcium salt of dodecylbenzensulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

In these application forms, the mixtures according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

USE EXAMPLES

EXAMPLE 1

Eradicative Action on Wheat Mildew

Wheat plants of the "Kanzler" variety were inoculated at the 3-leaf stage with wheat mildew (*Erysiphe graminis* var. *tritici*), and treated, when the fungal attack had reached about 5%, with the active ingredients in the stated concentrations. The amount of water employed was equivalent to 400 liters/ha. The plants were cultivated in the greenhouse for 20 days at from 18° to 22° C. The leaf area under attack was then assessed in percent. These figures were converted to degrees of effectiveness. The degree of effectiveness which the active ingredient mixture should be expected to have was determined in accordance with the Colby formula (Colby, S. R. "Calculating synergistic and antagonistic responses of herbicide combinations", Weeds, 15, p. 20-22, 1967) and compared with the degrees of effectiveness actually observed.

The values for the fungicidal action vary from experiment to experiment, because the heaviness of the fungal attack on the plants varied in the individual experiments, thus giving different figures for the fungicidal action. For this reason, only results within the same experiment can be compared with each other.

$$\text{Colby formula } E = X + Y - \frac{X \cdot Y}{100}$$

E = expected degree of effectiveness, expressed in % of the untreated control, when active ingredients A and B are used in concentrations m and n X = degree of effectiveness, expressed in % of the untreated control, when active ingredient A is used in a concentration of m Y = degree of effectiveness, expressed in % of the untreated control, when active ingredient B is used in a concentration of n

EXPERIMENT 1

*Erysiphe graminis* Test (wheat)

Eradicative

| Active ingredient | Active ingredient concentration in the spray liquor in % | Degree of effectiveness in % of untreated control |
| --- | --- | --- |
| Control (untreated) | — | 0 |
| I Compound a) (prior art) | 0.05 | 22 |
| II fenpropimorph (prior art) | 0.05 | 30 |
| III fenpropidin (prior art) | 0.05 | 33 |
| IV tridemorph (prior art) | 0.05 | 26 |
| Mixture according to the invention | | |
| I + II ratio   1:3 | 0.01 + 0.03 | 61 |
| I + III ratio  1:3 | 0.01 + 0.03 | 62 |
| I + IV ratio   1:3 | 0.01 + 0.03 | 58 |

These results show that 0.04% (0.01+0.03) of the mixture has a better fungicidal action than 0.05% of the individual active ingredients.

EXPERIMENT 2

*Erysiphe graminis* Test (wheat)

Eradicative

| Active ingredient | Active ingredient concentration in the spray liquor in % | Degree of effectiveness in % of the untreated control |
| --- | --- | --- |
| Control (untreated) | — | 0 |
| I compound a) (prior art) | 0.1 | 42 |
|  | 0.05 | 15 |
| II fenpropimorph (prior art) | 0.1 | 72 |
|  | 0.05 | 32 |

| Mixture according to the invention: | Observed degree of effectiveness | Calculated degree of effectiveness*) |
| --- | --- | --- |
| I + II  0.05 + 0.05 ratio 1:1 | 65 | 42.2 |
| I + II  0.1 + 0.1 ratio 1:1 | 100 | 83.8 |
| I + II  0.1 + 0.05 ratio 2:1 | 82 | 60.6 |
| I + II  0.05 + 0.1 ratio 1:2 | 95 | 73.2 |

*) calculated according to the Colby formula

We claim:
1. A fungicidal composition containing a synergistically fungicidally effective amount of a mixture consisting of
   a) 2-(1,2,4-triazol-1-ylmethyl)-2-(4-fluorophenyl)-3-(2-chlorophenyl)-oxirane of the formula I

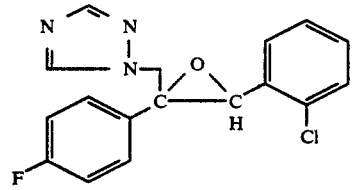

and b) 4-[3-(4-tert.-butylphenyl)-2-methylpropyl]-cis-2,6-dimethylmorpholine of the formula

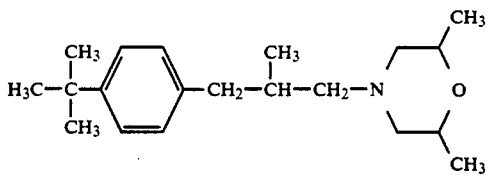

in a ratio of a:b of from 5:1 to 1:5.

2. A fungicidal composition of claim 1 wherein the ratio of a:b is from 3:1 to 1:3.

3. A fungicidal composition of claim 1 wherein the ratio of a:b is from 2:1 to 1:2.

4. A method for combating fungi, comprising applying a synergistically fungicidally effective amount of a mixture of claim 1 to the fungi, or to the materials, areas, plants or seed threatened by fungus attack.

5. A method for combating fungi, comprising applying a synergistically fungicidally effective amount of a mixture as set forth in claim 2 to the fungi, or to the materials, areas, plants or seed threatened by fungus attack.

6. A method for combating fungi, comprising applying a synergistically fungicidally effective amount of a mixture of claim 3 to the fungi, or to the materials, areas, plants or seed threatened by fungus attack.

* * * * *